United States Patent [19]

Boudakian

[11] Patent Number: 4,487,969

[45] Date of Patent: Dec. 11, 1984

[54] PRODUCTION OF M-FLUOROACETOPHENONE

[75] Inventor: Max M. Boudakian, Pittsford, N.Y.

[73] Assignee: Olin Corporation, Cheshire, Conn.

[21] Appl. No.: 429,762

[22] Filed: Sep. 30, 1982

[51] Int. Cl.$^3$ .......................................... C07C 49/303
[52] U.S. Cl. ................................... 568/316; 568/312; 568/323
[58] Field of Search ................ 568/312, 316, 308, 323

[56] References Cited

U.S. PATENT DOCUMENTS 3,954,734  5/1976  Doub et al. .......................... 568/312
4,075,252  2/1978  Boudakian .......................... 570/127

OTHER PUBLICATIONS

Evans et al., "J. Chemical Society", (1935), pp. 1167–1173.
Taft et al., "J. American Chemical Society", (1963), vol. 85, pp. 709–724.
Zweig et al., "J. Organic Chemistry", (1980), vol. 3597–3503.

Primary Examiner—Werren B. Lone
Attorney, Agent, or Firm—James B. Haglind; Donald F. Clements

[57] ABSTRACT

A process for the production of m-fluoroacetophenone comprises reacting m-aminoacetophenone with a diazotization agent in the presence of hydrogen fluoride. The diazonium fluoride compound produced is decomposed by heating to produce highly pure m-fluoroacetophenone in good yields.

6 Claims, No Drawings

PRODUCTION OF M-FLUOROACETOPHENONE

This application is related to the production of m-fluoroacetophenone. m-Fluoroacetophenone has previously been prepared by D. P. Evans et al, J. Chem. Soc., 1167 (1935), and R. W. Taft et al, J. Amer. Chem. Soc., 85, 709 (1963) using the classical 2-step Schiemann process. In this process, m-aminoacetophenone is diazotized to form a diazonium fluoroborate followed by decomposition by heating in accordance with the following reactions:

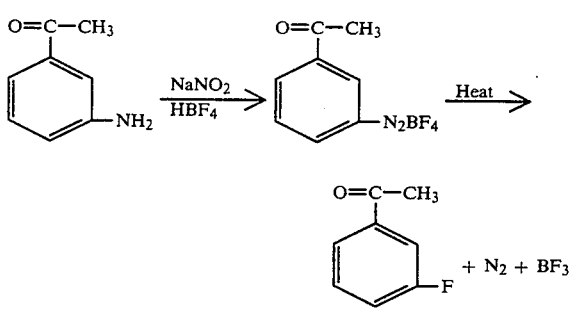

No indication of the yield is given in the publication by Evans et al, while the paper by Taft et al reports a yield of 19.6%.

Substitutive fluorination of acetophenone by reaction with cobaltic trifluoride in refluxing chloroform gave an inseparable mixture of fluorophenyl isomers having a ratio of 58% ortho, 28% meta and 14% para, as reported by A. Zweig et al, J. Organic Chem., 45, 3597 (1980).

There is, therefore, a need for a process for producing m-fluoroacetophenone in increased yields and of high purity.

It is an object of the present invention to provide a process for the production of m-fluoroacetophenone at increased yields.

Another object of the present invention is to provide a process for the production of m-fluoroacetophenone which is highly pure.

These and other objects of the invention are accomplished in a process for the production of m-fluoroacetophenone which comprises diazotizing m-aminoacetophenone by the reaction of a diazotization agent in the presence of hydrogen fluoride to produce a corresponding diazonium fluoride, and decomposing the diazonium fluoride to produce m-fluoroacetophenone.

In the novel process of the present invention, one of the reactants is m-aminoacetophenone, having the formula:

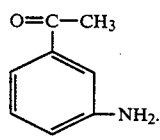

The reaction for the novel process of this invention is represented as follows:

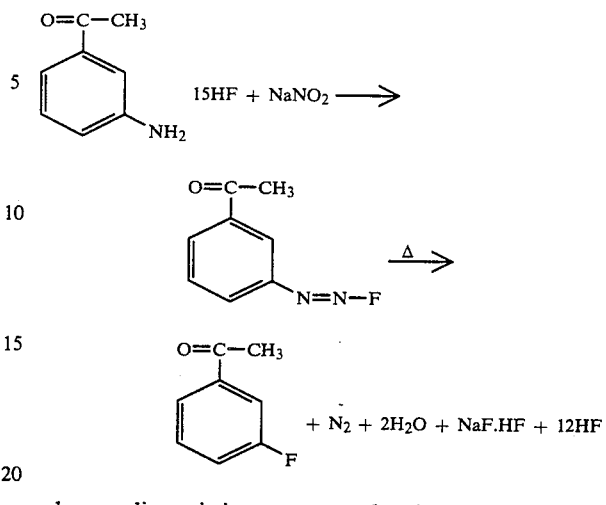

where sodium nitrite represents the diazotization agent.

The diazotization agents employed are those described in U.S. Pat. No. 4,075,252, issued Feb. 21, 1978, to M. M. Boudakian in which the diazotization-fluorination of aromatic primary amines and unsaturated heterocyclic primary amines is disclosed. Substituents on the aromatic and heterocyclic primary amines employed as the substrates in U.S. Pat. No. 4,075,252 do not include ketone groups.

The usual diazotization agents, namely, sodium nitrite, potassium nitrite, nitrous anhydride, nitrous acid and nitrosyl halides or nitrosyl halide complexes with HF may be employed in the reaction. The nitrous acid may be prepared in-situ by known methods, for example, by dissolving an alkali metal nitrite in excess hydrogen fluoride. From about 1.0 to about 1.5 moles of the diazotizing agent, and preferably about 1.0 to about 1.25 moles, are employed per mole of m-aminoacetophenone.

Hydrogen fluoride acts as the source of fluorine for the reaction. Suitably from about 2 moles up to about 30 moles of HF, preferably about 7.5 moles up to about 25 moles of HF, are employed per mole of substrate. Anhydrous HF is preferred because aqueous HF can cause corrosion to the equipment if not carefully controlled; however, aqueous solutions containing 70% HF up to anhydrous may be employed, if desired. The HF should be present in excess molar quantities over that necessary for the diazotization reaction because having too little HF present will cause the reaction to run out of control and endanger the safety of the operation. On the other hand, having too much HF present lowers the economic value of the process.

In a preferred embodiment of the present invention, a solution of hydrogen fluoride containing ammonium ions is utilized as the reaction medium. As used herein, the term "ammonium ions" is used in a general sense to indicate those ions formed by adding ammonium ion-generating compounds to the solution of hydrogen fluoride. Such compounds can be either ammonium salts such as ammonium fluoride and ammonium bifluoride; ammonium fluoride solvates like NH$_4$F.HF, NH$_4$.3HF, and NH$_4$F.5HF; aqueous or anhydrous ammonia or combinations thereof. Further sources of "ammonium ions" can be other soluble nonfluoride ammonium salts as described in detail below. The preferred source of ammonium ions is ammonium bifluoride because of its relatively low cost and ease of handling.

The structure of the compound or compounds formed when a source of ammonium ions is added to the HF medium has not been ascertained. It is believed that possibly an ammonium fluoride-HF complex is formed which is at least in part, one or more of the above solvates of ammonium fluoride and HF. The generalized formula for these solvates is $NH_4F \cdot xHF$, with x having one or more values in the range of about 1 to 10. It is known, for example, that when ammonium fluoride is added to HF, one or more stable solvates are formed, namely, $NH_4F \cdot 3HF$ having a melting point of $-23°$ C., and/or $NH_4F \cdot 5HF$ having a melting point of $-8°$ C. Also, it is known that when aqueous or anhydrous ammonia is added to HF, there is an instantaneous reaction to form ammonium fluoride, and quite possibly, these solvates are also produced. Likewise, when other ammonium salts like ammonium bifluoride and the like are used, it is also possible that the higher solvates are made. However, this is merely a theory and the present invention is not limited thereto. The important criterion is that some source of ammonium ions be added to the solution of HF in carrying out the present process.

The amount of ammonium ions is most conveniently expressed as a molar percent of the solution of hydrogen fluoride and this molar percent can range from about 0.5 to about 35 percent of the HF solution, preferably from about 2.5 to about 15 molar percent of the HF solution. In figuring this molar percent, only the moles of ammonium ions and those of HF are used; others such as anions of ammonium salts and the like are not used. For purposes of determining these percentages, where ammonium bifluoride is utilized for example, the bifluoride is regarded as contributing one mole of HF and one mole of ammonium ion per mole of the bifluoride.

As stated before, the ammonium ions can be alternatively formed by addition of non-fluoride ammonium salts instead of the addition of the above ammonium compounds to the HF. This is accomplished by adding any suitable soluble non-fluoride ammonium salt or salts to the HF so that the ammonium cation will react with hydrogen fluoride and may form said solvates. These salts should be soluble in the reaction medium so that the ammonium cation remains in solution. The following commercial ammonium salts are illustrative of those which may be employed:

Ammonium Acetate
Ammonium Bicarbonate
Ammonium Biborate or Pentaborate
Ammonium Bichromate
Ammonium Bromide
Ammonium Chloride
Ammonium Citrate
Ammonium Fluoroborate
Ammonium Molybdate or Dimolybdate
Ammonium Gluconate
Ammonium Lauryl Sulfate
Ammonium Nitrate
Ammonium Oxalate
Ammonium Persulfate
Ammonium Phosphate
Ammonium Silicofluoride
Ammonium Sulfamate
Ammonium Sulfate
Ammonium Thiosulfate
Ammonium Thiocyanate.

A basis and understanding of this embodiment of the invention wherein a non-fluoride ammonium salt in HF is used can be found in the treatise "Inorganic Chemistry in Liquid HF" by M. F. A. Dove and A. F. Clifford, Pergamon Press, New York, 1971, which states on page 156 that the halides of alkali metals, ammonium and substituted ammonium cations will be solvolyzed very readily to give solutions of their fluorides. On the basis of this teaching, soluble non-fluoride ammonium salts can be used to generate ammonium ions in the present invention provide they do not cause any appreciable hinderance or interference to the diazotizing or decomposing steps or will not be susceptible to diazotization themselves. And thus, it is to be understood that the ammonium compounds added to the HF solution can be in the form of either the above-noted ammonium fluoride compounds, ammonia (aqueous or anhydrous), or soluble non-fluoride ammonium salts.

The diazotization-fluorination process may be conducted in at least two basic ways; as a single step diazotization-decomposition or as a two-step process in which diazotization is effected at low temperature and then the reaction mixture is heated to effect decomposition.

In the two-step process, the diazotization is conducted at a temperature in the range of $-20°$ C. to about $10°$ C., preferably $-10°$ C. to about $10°$ C. This diazotization step is conducted in the usual manner by slowly adding the diazotization agent to a mixture of m-aminoacetophenone in HF. Where the ammonium salts are employed, they may be added initially to the mixture of HF and m-aminoacetophenone. Alternatively, the first step may be started without the addition of the ammonium ion-generating compounds and then these compounds are added to the reaction mixture part way through the first step. Thereafter, the reaction mixture is heated to the decomposition temperature which is the temperature at which nitrogen evolution becomes substantially complete. Generally, depending on which diazonium fluoride intermediate is being decomposed, this will occur by the time the temperature reaches the reflux temperature of the reaction mixture, namely, about $40°$ C.–$50°$ C. In other instances, higher temperatures are required and usually these may be attained by heating under pressure or evaporating solvent until the desired temperature is reached. It should be noted that "decomposition" is defined herein as the removal of $N_2$ from the diazonium fluoride, preferably as shown by increased temperature. However, other methods, if applicable, could be used.

If it is desired to conduct the reaction in a single step, the diazotization agent is dissolved in one portion of the HF, the m-aminoacetophenone in another. The ammonium ions may be added to one or both HF portions. The diazotization agent in HF is then added slowly to the m-aminoacetopheone in HF at a temperature above the decomposition temperature of the diazonium fluoride. Suitable temperatures for the one-step reaction thus fall within the range from about $15°$ C. to about $50°$ C., that is, from as low as the temperature at which decomposition begins to the reflux temperature of the reaction mixture. If that is not sufficiently high, then the reaction can be conducted under pressure to attain higher temperatures.

It is apparent from the foregoing discussion that, depending on the technique for conducting the reaction, and on the particular substrate, diazotization temperatures may vary within the range of $-20°$ C. up to about $50°$ C. Decomposition temperatures may vary in the range of from about 15° C. to about 350° C., preferably 15° C. to about 100° C.

While it is preferable to operate at atmospheric pressure, lower or higher pressures may be used as desired, for example, those in the range of from about 0.5 to 50 atmospheres, advantageously from about 0.8 to about 1.5 atmospheres.

Where either a one or two-step process is employed, the decomposition time will vary with the speed at which the diazotization agent is added and/or with the temperature. Where a heat exchange medium is used, the decomposition is instantaneous. Where a two-step process is utilized, the decomposition time will depend on the speed at which temperature is increased; and, in the one-step process, on the speed at which the diazotization agent is added to the m-aminoacetophenone/HF mixture. Decomposition time may thus vary from about 0.5 seconds up to about 25 hours.

The present process can be carried out in any conventional chemical reactor which is suitable for this purpose. The reactor can be made out of stainless steel or plastics such as chlorotrifluoroethylene or tetrafluoroethylene polymers. The preferred is a conventional type 304 stainless steel reactor.

m-Fluoroacetophenone produced by the novel process of the present invention is used as a chemical intermediate in pharmaceutical applications such as the preparation of broad spectrum antibacterial agents as described in U.S. Pat. No. 3,954,734, issued May 4, 1976, to L. Doub et al; or the preparation of drugs for treating heart and circulatory diseases as described in French Pat. No. M8074, issued July 15, 1970, to Deutsche Gold- and Silver-Scheideanstaltvorm Roesler (Chem. Absts. 77, 34146g, 1972).

While the novel process of the present invention has been described for the preparation of m-fluoroacetophenone, it will be recognized that the process can also be used to produce other m-fluorophenyl-1-alkanones such as m-fluorophenylpropanone, m-fluorophenylisopropanone, m-fluorophenylbutanone, m-fluorophenylisobutanone, m-fluorophenylpentanone as well as higher phenyl ketones.

The following EXAMPLE further illustrates the invention.

EXAMPLE m-Fluoroacetophenone

A 2 liter stainless steel 304 reactor cooled at (−)10° C. was successively charged with anhydrous HF (20 moles; 400 g.), ammonium bifluoride (1.5 moles; 85.5 g.) and m-aminoacetophenone (1.0 mole; 135.2 g.). Diazotization was accomplished by the addition of sodium nitrite (1.2 moles; 82.8 g.).

The diazonium fluoride was then decomposed by heating at 23°–57° C. during a 7.75 hour period. After the decomposition was complete, as evidenced by no further gas evolution, the mixture was cooled to 0° C. and neutralized by addition to 29% NH$_4$OH.

Steam distillation of the reaction mixture gave 83.5 g. of an organic layer, $n_D^{20}$ 1.5090; VPC: 99.74% m-fluoroacetophenone (0.605 mole; 60.5% in-hand yield).

What is claimed is:

1. A process for the production of m-fluoroacetophenone which comprises reacting m-aminoacetophenone with a diazotization agent and hydrogen fluoride to produce a corresponding diazonium fluoride; and decomposing the diazonium fluoride to produce m-fluoroacetophenone.

2. The process of claim 1 in which said diazotization agent is selected from the group consisting of sodium nitrite, potassium nitrite, nitrous anhydride, nitrous acid, nitrosyl halide, and a complex of a nitrosyl halide with hydrogen fluoride.

3. The process of claim 2 wherein ammonium ions are also provided by adding to the hydrogen fluoride an ammonium ion generating compound selected from the group of anhydrous ammonia, aqueous ammonia, ammonium fluoride, ammonium bifluoride, a solvate of ammonium fluoride with hydrogen fluoride, a soluble non-fluoride ammonium salt, and combinations thereof.

4. The process of claim 3 in which said diazonium fluoride is decomposed by heating at a temperature in the range of from about 15° C. to about 100° C.

5. The process of claim 4 wherein said diazotization and decomposition steps are conducted in a solution of hydrogen fluoride containing from about 2.5 to about 15 mole percent of ammonium ion, and from about 7.5 to about 25 moles of hydrogen fluoride are present per one mole of said m-aminoacetophenone.

6. The process of claim 5 wherein said ammonium ions are formed by adding ammonium bifluoride to said hydrogen fluoride.

* * * * *